(12) United States Patent
Thornton

(10) Patent No.: US 8,573,224 B2
(45) Date of Patent: Nov. 5, 2013

(54) CUSTOM-MOLDED ORAL APPLIANCE AND METHOD OF FORMING

(75) Inventor: W. Keith Thornton, Dallas, TX (US)

(73) Assignee: Airway Technologies, LLC, Carrollton, TX (US)

( * ) Notice: Subject to any disclaimer, the term of this patent is extended or adjusted under 35 U.S.C. 154(b) by 369 days.

(21) Appl. No.: 12/892,217

(22) Filed: Sep. 28, 2010

(65) Prior Publication Data
US 2011/0088701 A1    Apr. 21, 2011

Related U.S. Application Data

(60) Provisional application No. 61/252,302, filed on Oct. 16, 2009.

(51) Int. Cl.
*A61F 5/56*    (2006.01)

(52) U.S. Cl.
USPC .......... 128/848; 128/859; 128/861; 128/862; 433/214

(58) Field of Classification Search
USPC .......... 128/848, 859, 861–862; 433/37, 48, 6, 433/71, 214
See application file for complete search history.

(56) References Cited

U.S. PATENT DOCUMENTS

| | | |
|---|---|---|
| 690,663 A | 1/1902 | Pratt |
| 746,869 A | 12/1903 | Moulton |
| 774,446 A | 11/1904 | Moulton |
| 885,196 A | 4/1908 | Steil |
| 893,213 A | 7/1908 | Whiteway |
| 955,562 A | 4/1910 | Thomas |
| 996,783 A | 7/1911 | Moreau |
| 1,076,534 A | 10/1913 | Wallen |
| 1,146,264 A | 7/1915 | Kelly |
| 1,483,694 A | 2/1924 | Stukey |
| 1,592,345 A | 7/1926 | Drager |
| 1,649,664 A | 11/1927 | Carter |

(Continued)

FOREIGN PATENT DOCUMENTS

| | | |
|---|---|---|
| DE | 2 320 501 | 11/1974 |
| DE | 29506512.5 | 7/1995 |

(Continued)

OTHER PUBLICATIONS

Personally Moulded Sleep Apnea Masks, http:/;web.archive.org/web/20030618145716/ www.sleepapneamasks.com.au/default.asp, downloaded Aug. 17, 2009 (2 pages).

(Continued)

*Primary Examiner* — Patricia Bianco
*Assistant Examiner* — Camtu Nguyen
(74) *Attorney, Agent, or Firm* — Baker Botts L.L.P.

(57) ABSTRACT

A method for forming a custom-molded oral appliance for positioning a user's jaw proximate to centric occlusion is disclosed. The method includes heating a thin sheet of material comprising a polycaprolactone polymer. The thin sheet of material is positioned within the user's mouth. The user's jaw is positioned proximate to centric occlusion. The thin sheet of material is molded around at least respective portions of the user's upper and lower dental arches such that each of the respective portions of the user's upper and lower dental arches form respective impressions on opposite sides of the thin sheet of material. The thin sheet of material is transitioned to a substantially non-deformable state.

15 Claims, 3 Drawing Sheets

(56) References Cited

U.S. PATENT DOCUMENTS

| | | |
|---|---|---|
| 1,674,336 A | 6/1928 | King |
| 1,675,202 A | 6/1928 | Warne |
| 1,679,748 A | 8/1928 | Stratton |
| 2,171,695 A | 9/1939 | Harper |
| 2,178,128 A | 10/1939 | Waite |
| 2,424,533 A | 7/1947 | Faires |
| 2,505,028 A | 4/1950 | Boeger |
| 2,521,039 A | 9/1950 | Carpenter |
| 2,521,084 A | 9/1950 | Oberto |
| 2,531,222 A | 11/1950 | Kesling |
| 2,574,623 A | 11/1951 | Clyde |
| 2,590,118 A | 3/1952 | Oddo, Jr. |
| 2,627,268 A | 2/1953 | Leppich |
| 2,833,278 A | 5/1958 | Ross |
| 2,867,212 A | 1/1959 | Nunn, Jr. |
| 2,882,893 A | 4/1959 | Godfroy |
| 3,037,501 A | 6/1962 | Miller |
| 3,064,354 A | 11/1962 | Pos |
| 3,107,668 A | 10/1963 | Thompson |
| 3,124,129 A | 3/1964 | Grossberg |
| 3,132,647 A | 5/1964 | Corniello |
| 3,219,033 A | 11/1965 | Wallshein |
| 3,277,892 A | 10/1966 | Tepper |
| 3,312,216 A | 4/1967 | Wallshein |
| 3,321,832 A | 5/1967 | Weisberg |
| 3,360,860 A | 1/1968 | Roland |
| 3,434,470 A | 3/1969 | Strickland |
| 3,457,916 A | 7/1969 | Wolicki |
| 3,513,838 A | 5/1970 | Foderick et al. |
| 3,522,805 A | 8/1970 | Wallshein |
| 3,690,004 A | 9/1972 | Frush |
| 3,854,208 A | 12/1974 | Arant |
| 3,864,832 A | 2/1975 | Carlson |
| 3,871,370 A | 3/1975 | McDonald |
| 3,882,601 A | 5/1975 | Jahn |
| 3,884,226 A | 5/1975 | Tepper |
| 4,016,650 A | 4/1977 | Leusner et al. |
| 4,026,024 A | 5/1977 | Tradowsky |
| 4,114,614 A | 9/1978 | Kesling |
| 4,169,473 A | 10/1979 | Samelson |
| 4,182,312 A | 1/1980 | Mushabac |
| 4,227,877 A | 10/1980 | Tureaud et al. |
| 4,258,710 A | 3/1981 | Reber |
| 4,289,127 A | 9/1981 | Nelson |
| 4,304,227 A | 12/1981 | Samelson |
| 4,376,628 A | 3/1983 | Aardse |
| 4,382,783 A | 5/1983 | Rosenberg |
| 4,419,992 A | 12/1983 | Chorbajian |
| 4,433,956 A | 2/1984 | Witzig |
| 4,439,147 A | 3/1984 | Magill et al. |
| 4,439,149 A | 3/1984 | Devincenzo |
| 4,454,090 A | 6/1984 | Saumell |
| 4,495,945 A | 1/1985 | Liegner |
| 4,505,672 A | 3/1985 | Kurz |
| 4,530,662 A | 7/1985 | Andersson et al. |
| 4,553,549 A | 11/1985 | Pope et al. |
| 4,568,280 A | 2/1986 | Ahlin |
| 4,569,342 A | 2/1986 | von Nostitz |
| 4,593,686 A | 6/1986 | Lloyd et al. |
| 4,602,905 A | 7/1986 | O'Keefe, III |
| 4,639,220 A | 1/1987 | Nara et al. |
| 4,668,188 A | 5/1987 | Wolfenson et al. |
| 4,669,459 A | 6/1987 | Spiewak et al. |
| 4,676,240 A | 6/1987 | Gardy |
| 4,715,368 A | 12/1987 | George |
| 4,741,696 A | 5/1988 | Cetlin |
| 4,773,853 A | 9/1988 | Kussick |
| 4,784,123 A | 11/1988 | Robeson |
| 4,799,500 A | 1/1989 | Newbury |
| 4,858,605 A | 8/1989 | Levy |
| 4,862,903 A | 9/1989 | Campbell |
| 4,892,478 A | 1/1990 | Tateosian et al. |
| 4,901,737 A | 2/1990 | Toone |
| 4,932,867 A | 6/1990 | Ueno |
| 4,955,393 A | 9/1990 | Adell |
| RE33,442 E | 11/1990 | George |
| 5,003,994 A | 4/1991 | Cook |
| 5,011,407 A | 4/1991 | Pelerin |
| 5,018,533 A | 5/1991 | Hawkins |
| 5,026,278 A | 6/1991 | Oxman et al. |
| 5,028,232 A | 7/1991 | Snow |
| 5,040,976 A | 8/1991 | Ubel, III et al. |
| 5,042,506 A | 8/1991 | Liberati |
| 5,046,512 A | 9/1991 | Murchie |
| 5,052,409 A | 10/1991 | Tepper |
| 5,055,039 A | 10/1991 | Abbatte et al. |
| 5,056,534 A | 10/1991 | Wright |
| 5,064,371 A | 11/1991 | Smeltzer |
| 5,066,231 A | 11/1991 | Oxman et al. |
| 5,078,600 A | 1/1992 | Austin |
| 5,092,346 A | 3/1992 | Hays et al. |
| 5,103,838 A | 4/1992 | Yousif |
| 5,112,225 A | 5/1992 | Diesso |
| 5,117,816 A | 6/1992 | Shapiro et al. |
| 5,154,184 A | 10/1992 | Alvarez |
| 5,154,609 A | 10/1992 | George |
| 5,183,057 A | 2/1993 | Syrop et al. |
| 5,188,529 A | 2/1993 | Lüth |
| 5,190,457 A | 3/1993 | Schreinemakers |
| 5,213,498 A | 5/1993 | Pelerin |
| 5,265,595 A | 11/1993 | Rudolph |
| 5,267,862 A | 12/1993 | Parker |
| 5,277,202 A | 1/1994 | Hays |
| 5,284,161 A | 2/1994 | Karell |
| 5,313,960 A | 5/1994 | Tomasi |
| 5,316,020 A | 5/1994 | Truffer |
| 5,320,533 A | 6/1994 | Lee |
| 5,336,086 A | 8/1994 | Simmen et al. |
| 5,365,945 A | 11/1994 | Halstrom |
| 5,370,533 A | 12/1994 | Bushnell |
| 5,373,859 A | 12/1994 | Forney |
| 5,409,017 A | 4/1995 | Lowe |
| 5,415,544 A | 5/1995 | Oxman et al. |
| 5,427,117 A | 6/1995 | Thornton |
| 5,474,060 A | 12/1995 | Evans |
| 5,499,633 A | 3/1996 | Fenton |
| 5,503,552 A | 4/1996 | Diesso |
| 5,537,994 A | 7/1996 | Thornton |
| 5,551,872 A | 9/1996 | Mena |
| 5,562,106 A * | 10/1996 | Heeke et al. .................. 128/848 |
| 5,562,449 A | 10/1996 | Jacobs et al. |
| 5,566,683 A | 10/1996 | Thornton |
| 5,570,704 A | 11/1996 | Buzzard et al. |
| 5,582,517 A | 12/1996 | Adell |
| 5,616,027 A * | 4/1997 | Jacobs et al. .................... 433/37 |
| 5,678,567 A | 10/1997 | Thornton et al. |
| 5,681,164 A | 10/1997 | Bass |
| 5,718,244 A | 2/1998 | Thornton |
| 5,720,302 A | 2/1998 | Belfer |
| 5,755,219 A | 5/1998 | Thornton |
| 5,807,100 A | 9/1998 | Thornton |
| 5,829,441 A | 11/1998 | Kidd et al. |
| 5,846,082 A | 12/1998 | Thornton |
| 5,891,372 A | 4/1999 | Besset et al. |
| 5,954,048 A | 9/1999 | Thornton |
| 5,983,892 A | 11/1999 | Thornton |
| 6,012,919 A | 1/2000 | Cross, III et al. |
| 6,083,442 A | 7/2000 | Gabilly |
| 6,109,265 A | 8/2000 | Frantz et al. |
| 6,155,262 A | 12/2000 | Thornton et al. |
| 6,209,542 B1 | 4/2001 | Thornton |
| 6,247,926 B1 | 6/2001 | Thornton |
| 6,305,376 B1 | 10/2001 | Thornton |
| 6,314,960 B1 * | 11/2001 | Vines ............................ 128/859 |
| 6,318,997 B1 | 11/2001 | Mayweather |
| 6,325,064 B1 | 12/2001 | Thornton |
| 6,374,824 B1 | 4/2002 | Thornton |
| 6,405,729 B1 | 6/2002 | Thornton |
| 6,450,167 B1 | 9/2002 | David et al. |
| 6,464,924 B1 | 10/2002 | Thornton |
| 6,516,805 B1 | 2/2003 | Thornton |
| 6,536,439 B1 | 3/2003 | Palmisano |
| 6,571,798 B1 | 6/2003 | Thornton |
| 6,604,527 B1 | 8/2003 | Palmisano |

(56) References Cited

U.S. PATENT DOCUMENTS

| | | | |
|---|---|---|---|
| 6,675,802 B1 | 1/2004 | Thornton | |
| 6,758,212 B2 | 7/2004 | Swann | |
| 6,769,910 B1 | 8/2004 | Pantino | |
| 6,845,774 B2 | 1/2005 | Gaskell | |
| 6,848,905 B2* | 2/2005 | Jacobs et al. | 433/37 |
| 6,860,736 B2* | 3/2005 | Allred et al. | 433/80 |
| 6,877,513 B2 | 4/2005 | Scarberry et al. | |
| 7,174,895 B2 | 2/2007 | Thornton et al. | |
| 7,597,103 B2 | 10/2009 | Thornton et al. | |
| 7,650,885 B2 | 1/2010 | Paoluccio et al. | |
| 7,677,889 B2 | 3/2010 | Thornton | |
| 7,721,741 B2 | 5/2010 | Thornton | |
| 7,748,386 B2 | 7/2010 | Thornton | |
| 7,823,590 B2 | 11/2010 | Bibi et al. | |
| 7,832,403 B2 | 11/2010 | Halstrom | |
| 7,909,035 B2 | 3/2011 | Thornton | |
| 8,020,276 B2 | 9/2011 | Thornton | |
| 2002/0000230 A1 | 1/2002 | Gaskell | |
| 2002/0139366 A1 | 10/2002 | Gaschke | |
| 2003/0217753 A1 | 11/2003 | Thornton | |
| 2003/0234022 A1 | 12/2003 | Belfer | |
| 2004/0079374 A1 | 4/2004 | Thornton | |
| 2004/0226563 A1 | 11/2004 | Xu et al. | |
| 2004/0237965 A1 | 12/2004 | Bibi et al. | |
| 2005/0028827 A1 | 2/2005 | Halstrom | |
| 2005/0034733 A1 | 2/2005 | Liddle et al. | |
| 2005/0268914 A1 | 12/2005 | Paoluccio et al. | |
| 2007/0125388 A1 | 6/2007 | Thornton et al. | |
| 2007/0235037 A1 | 10/2007 | Thornton | |
| 2008/0006273 A1 | 1/2008 | Thornton | |
| 2008/0006274 A1 | 1/2008 | Thornton | |
| 2008/0032256 A1 | 2/2008 | Thornton | |
| 2008/0127984 A1 | 6/2008 | Thornton | |
| 2008/0295850 A1 | 12/2008 | Lesniak | |
| 2009/0130624 A1 | 5/2009 | Sun et al. | |
| 2010/0065067 A1 | 3/2010 | Lee | |
| 2011/0168187 A1 | 7/2011 | Nelissen | |

FOREIGN PATENT DOCUMENTS

| | | |
|---|---|---|
| EP | 0 312 368 A1 | 4/1989 |
| EP | 0 359 135 A1 | 3/1990 |
| GB | 1 569 129 | 6/1980 |
| GB | 2 072 567 A | 10/1981 |
| WO | WO 91/12777 | 9/1991 |
| WO | WO 97/25010 | 7/1997 |
| WO | WO 98/26736 | 6/1998 |
| WO | WO 98/46177 | 10/1998 |

OTHER PUBLICATIONS

European Patent Office, Application No. 03 809 555.0-125, Applicant: W. Keith Thornton, 3 pages, dated Feb. 23, 2010; 4 pages.
PCT, Notification of Transmittal of the International Search Report and the Written Opinion of the International Searching Authority, or the Declaration, International Application No. PCT/US2011/039231, filing date Jun. 6, 2011 (11 pgs).
Japanese Patent Office re patent application 2004-500750, mailed Oct. 14, 2008.
Australian Office Action re patent application No. 2007/243957 dated Mar. 9, 2012.
PCT Intl. Searching Authority, Invitation to pay Add'l Fees, Re PCT/US2012/028885 mailed May 30, 2012 (0306 Foreign).
PCT Intl. Searching Authority, Invitation to pay Add'l Fees, Re PCT/US2012/032407 mailed May 30, 2012.
Canadian IPO patent application No. 2,502,280 dated Feb. 23, 2010.
Mayo Clinic Health Letter; Reliable Information for a Healthier Life; *Snoring: Laser Surgery Joins Battle to Restore Peace and Quiet*; vol. 13, No. 7, 8 pages, Jul. 1995.
Photocopies of 2-piece dental device manufactured by Currie-Gibson Dental Lboratory, Inc., prior to Apr. 13, 1993, 5 pages.
Farrar, et al, *A Clinical Outline of Temporomandibular Joint Diagnosis and Treatment*, Normandie Study Group for TMJ Dysfunction, 3 pages, 1983.
Professional Positioners; *Dedicated to Excellence* brochure, 3 pages.
Great Lakes Orthodontics, Ltd.; *Nocturnal Airway Patency Applicance*; 2 pages.
Schmidt-Nowara, et al.; An American Sleep Disorders Association Review; *Oral Appliances for the Treatment of Snoring and Obstructive Sleep Apnea: A Review*; pp. 501-510, 1995.
George, Peter; *Treatment of Snoring and Obstructive Sleep Apnea with a Dental Device*; 5 pages, Jul.-Aug. 1993.
Database WOI, Section PQ, Week 9039, Derwent Publications, Ltd., London, GB; XP-002116355 Abstract—*Surgical Mouth Air Duct*; 1 page, Dec. 15, 1989.
PCT Notification of Transmittal of The International Search Report or the Declaration for International Application No. PCT/US97/08708, 4 pages, Aug. 12, 1997.
PCT Invitation to Pay Additional Fees for International Application No. PCT/US03/13705, 6 pages, Oct. 10, 2003.
PCT, Notification of Transmittal of the International Search Report and the Written Opinion of the International Searching Authority, or the Declaration, PCT/US07/02736, 10 pages, Date Mailed: Oct. 26, 2007.
PCT, Notification of Transmittal of the International Search Report and the Written Opinion of the International Searching Authority, or the Declaration, PCT/US2010/051136, 10 pages, Date Mailed Mar. 4, 2011.
Craig, William H., et al.; "Skeletal class II treatment with the Chateau appliance," The Journal of Pedondontics (vol. 11:120); pp. 120-138, 1987.
Samuel T. Kuna, M.D., et al., "Effect of Progressive Mandibular Advancement on Pharyngeal Airway Size in Anesthetized Adults," National Institute of Health; NIH Public Access Author Manuscript; Published Oct. 2008; Anesthesiology; 109(4); 16 pages.
PCT Notification of Transmittal of the International Search Report and the Written Opinion of the International Searching Authority, or the Declaration; mailed Jul. 13, 2012; International app No. PCT/US2012/032407; 18 pages.

\* cited by examiner

CUSTOM-MOLDED ORAL APPLIANCE AND METHOD OF FORMING

RELATED APPLICATION

This application claims priority to U.S. Provisional Application No. 61/252,302 filed Oct. 16, 2009.

TECHNICAL FIELD

This invention relates generally to oral appliances, and more particularly to a device and method for forming a custom-molded oral appliance.

BACKGROUND

Many people experience breathing problems on a recurring basis, which often result in sleep disordered breathing (e.g., difficulty sleeping, snoring, or other more serious conditions, such as obstructive sleep apnea). Various devices may be used to adjustably position a user's lower jaw relative to the user's upper jaw in order to open the breathing passageway more fully and thereby allow easier breathing through the nose and mouth. In certain cases, prolonged use of a device that adjustably positions a lower jaw relative to an upper jaw may leave the user's jar in an unnatural position or temporarily modify the user's bite once the device is removed.

Overview

According to one embodiment, a method for forming a custom-molded oral appliance for positioning a user's jaw proximate to centric occlusion is disclosed. The method includes heating a thin sheet of material comprising a polycaprolactone polymer. The thin sheet of material is positioned within the user's mouth. The user's jaw is positioned proximate to centric occlusion. The thin sheet of material is molded around at least respective portions of the user's upper and lower dental arches such that each of the respective portions of the user's upper and lower dental arches form respective impressions on opposite sides of the thin sheet of material. The thin sheet of material is transitioned to a substantially non-deformable state.

Certain embodiments may provide one or more technical advantages. For example, certain embodiments may provide for an oral appliance that facilitates the repositioning of a user's jaw. Particular embodiments may be readily customized to fit the particular features of a user's mouth. Various embodiments may provide for the efficient and relatively inexpensive formation of a jaw-repositioning oral appliance consisting entirely or substantially of a polycaprolactone polymer. Particular oral appliances formed from one or more polycaprolactone polymers may provide a deformable structure at an elevated temperature that is safe for use in a user's mouth. The deformable structure may be molded within the user's mouth to a desired shape and may also be wholly or partially transitioned to a substantially non-deformable state while within the user's mouth. Particular embodiments may be capable of retaining a desired shape over time even after multiple uses within the user's mouth. In addition, particular oral appliances formed from one or more polycaprolactone polymers may be thinned at certain locations to 0.1 mm or less and may be capable of retaining a molded shape at those thinned locations. Certain embodiments may provide all, some, or none of these advantages. Certain embodiments may provide one or more other technical advantages, one or more of which may be apparent to those skilled in the art from the figures, descriptions, and claims included herein.

BRIEF DESCRIPTION OF THE DRAWINGS

For a more complete understanding of the present invention and certain of its advantages, reference is now made to the following description, taken in conjunction with the accompanying drawings, in which.

DESCRIPTION OF EXAMPLE EMBODIMENTS

The present disclosure generally relates to a custom-molded oral appliance for repositioning a user's jaw and a method of forming the same. In certain embodiments, the oral appliance may be used to position a lower jaw relative to an upper jaw, such that the jaws are aligned at or proximate to centric occlusion. It should be understood at the outset, however, that although example embodiments are explained in the context of a custom-fit oral appliance for repositioning a user's jaw, various embodiments may provide for an oral appliance for use in a variety of alternative applications. Additionally, the present disclosure should in no way be limited to the example embodiments, drawings, and techniques disclosed.

Figure 2:
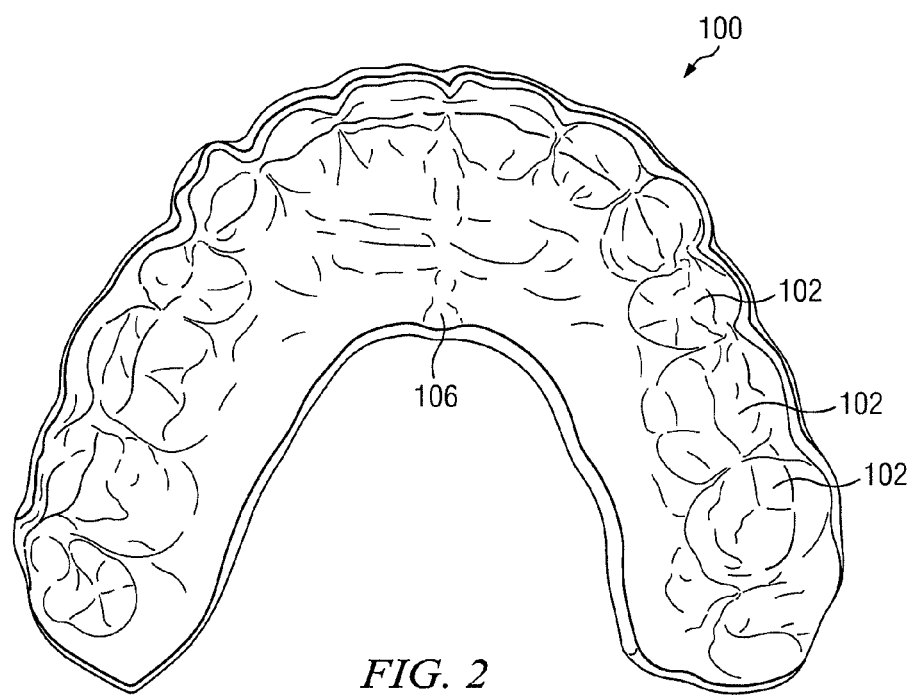
Figure 3:
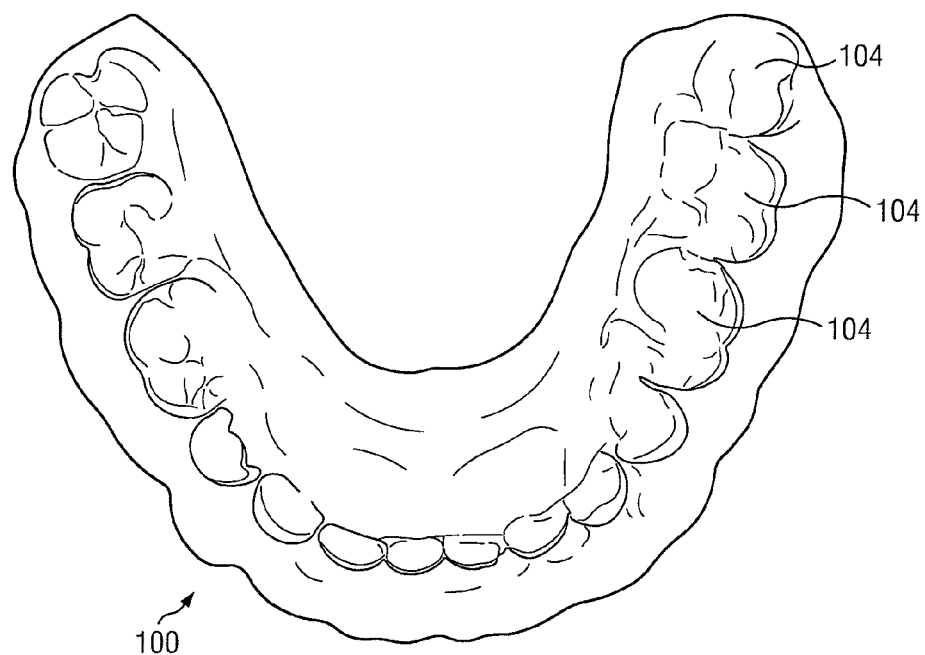

FIGS. 1 through 4 illustrate various views of an oral appliance 100 according to one embodiment. As shown in FIGS. 1 through 4, oral appliance 100 may be formed to custom-fit various features of a particular user's mouth at centric occlusion. For example, oral appliance 100 may include impressions 102 of at least a portion of a user's upper dentition, impressions 104 of at least a portion of a user's lower dentition, and impressions 106 of at least a portion of a user's pallet. FIG. 2 is a top view illustrating example impressions 102 that may be made by dentition of the user's upper dental arch and impressions 106 of a portion of the user's pallet. FIG. 3 is a bottom view illustrating example impressions 104 that may be made by dentition of the user's lower dental arch.

Figure 1:
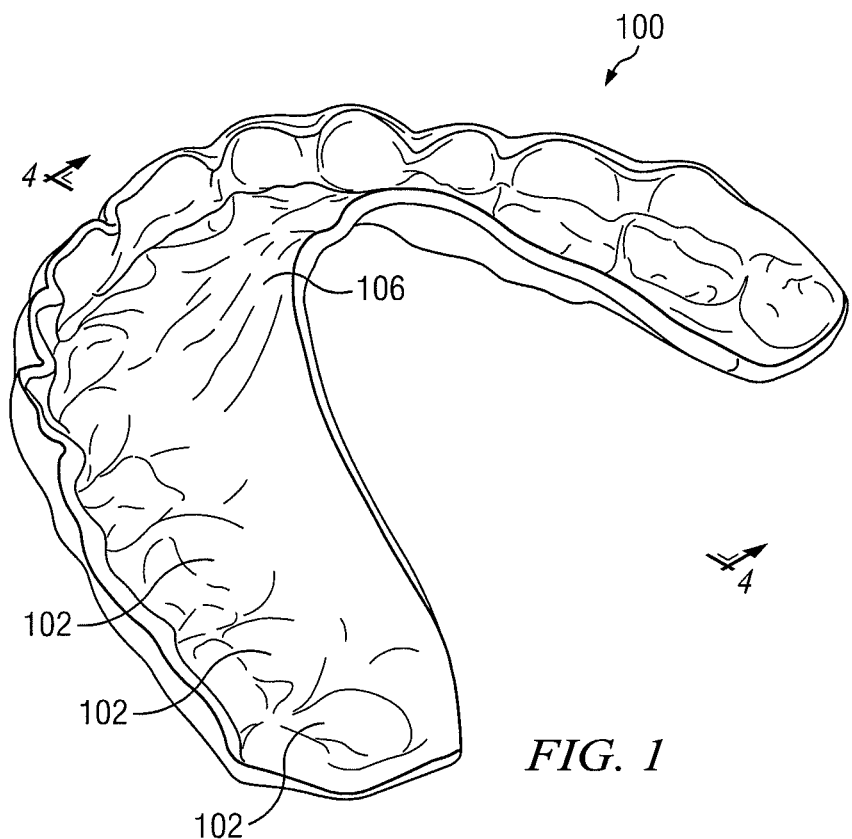
FIGS. 1 through 4 illustrate various views of an oral appliance according to an example embodiment.
Figure 4:
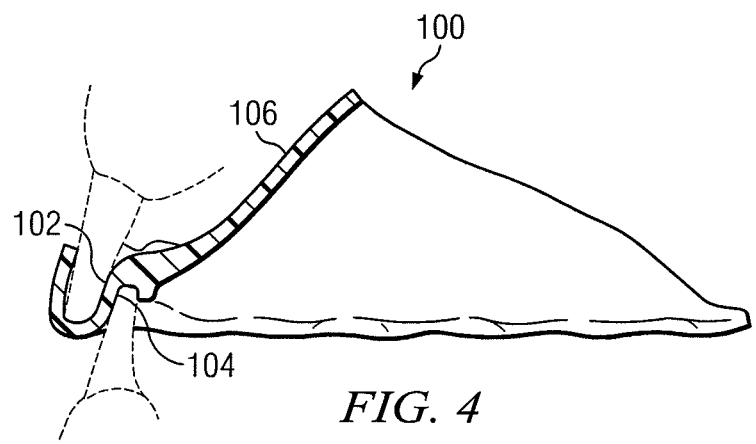

In certain embodiments, oral appliance 100 may be formed to custom-fit multiple surfaces of the lower and/or upper dental arches including, for example, the dental surfaces generally described as incisal, occlusal, mesial, distil, labial, palatal, lingual, etc. In some embodiments, oral appliance 100 may be configured to cover only a portion of some of these teeth surfaces while leaving other surfaces exposed. For example, FIG. 4 shows an oral appliance 100 configured to cover, when in operation, only a portion of the labial surfaces of the lateral and medial incisors. Although FIGS. 1 through 4 show an oral appliance 100 customized to fit substantially all of the upper and lower dental arches, in alternative embodiments oral appliance 100 may be configured to custom-fit respective portions, but not all, of the upper and/or lower dental arches.

In particular embodiments, oral appliance 100 may have a minimum thickness of approximately 0.2 mm or less. For example, particular oral appliances 100 may be approximately 0.1 mm or thinner at locations configured to be positioned between two opposing molars of a user; however, any suitable thickness may be used. In certain embodiments, oral appliance 100 may be sufficiently narrowed in certain places such that the user's jaw closely approximates centric occlusion when oral appliance 100 is positioned in the user's mouth. In a particular embodiment, oral appliance 100 may be 0.1 mm thick or less in one or more areas between the most posterior teeth covered by oral appliance 100.

In operation, an oral appliance 100 custom-fitted to a particular user may be inserted into the user's mouth. As the user bites down, oral appliance 100 may facilitate repositioning the user's jaw according to a desired alignment, such as, for example, centric occlusion and/or the user's natural bite prior to treatment. According to a particular embodiment, oral appliance 100 may be used to reposition a user's jaw after the jaw is intentionally misaligned for a prolonged period of time. For example, many people with sleep disordered breathing (e.g., difficulty sleeping, snoring, or other more serious conditions, such as obstructive sleep apnea) may use an oral appliance or other device that adjustably positions the lower jaw relative to the upper jaw in order to open the breathing passageway more fully and thereby allow easier breathing through the nose and mouth. When such a system is used for a prolonged period (e.g., throughout the night), it may become difficult and/or uncomfortable for the user to reposition his or her jaw to its natural position. Oral appliance 100 may be configured to assist a user to reposition or realign the user's jaw, with minimal effort, according to a more optimal or natural position (e.g., centric occlusion and/or the user's natural bite).

Figure 5:
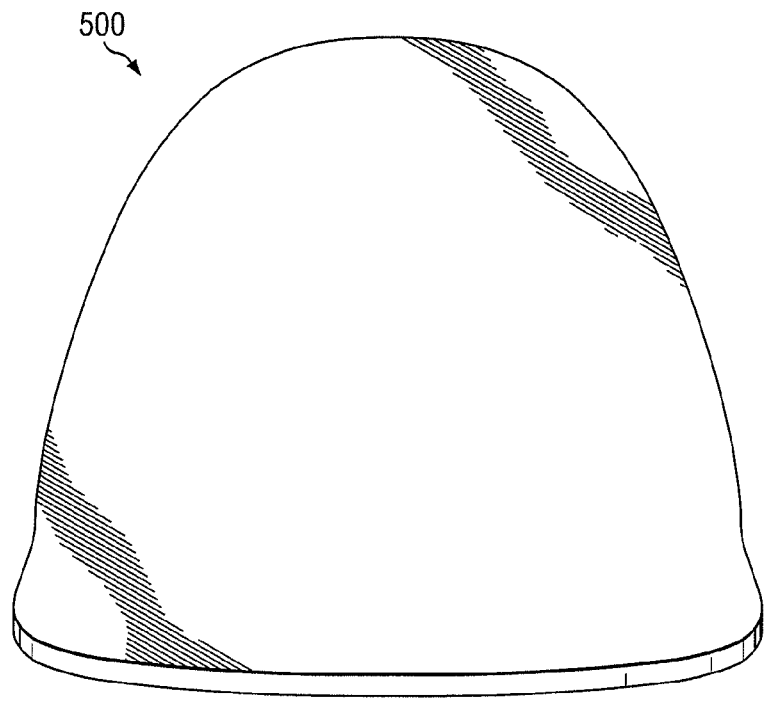
FIG. 5 illustrates a deformable blank that may be used in the formation of the oral appliance of FIGS. 1 through 4 according to an example embodiment.

FIG. 5 illustrates a deformable blank 500 that may be used in the formation of oral appliance 100 according to an example embodiment. Deformable blank 500 may have any suitable shape and/or dimensions. As shown in FIG. 5, for example, deformable blank 500 may be in the shape of a filled arc, which in some cases may facilitate custom-fitting oral appliance 100 to the user's upper and lower dental arches with minimal waste; however, any suitable shape may be used including, for example, a U-shape, a shape that is substantially square, a shape that is substantially rectangle with or without rounded corners, or any other suitable shape. In various embodiments, deformable blank 500 may have an initial thickness in the range between approximately 0.1 and approximately 0.2 inches. In a particular embodiment, deformable blank 500 may have a thickness of approximately 0.125 inches.

In this example, deformable blank 500 may be sufficiently large to enable the molding of deformable blank 500 to multiple surfaces of the entire upper and lower dental arches including, for example, the dental surfaces generally described as incisal, occlusal, mesial, distil, labial, palatal, lingual, etc. Although the deformable blank 500 of FIG. 5 is sufficiently large to cover the entire upper and lower dental arches, in alternative embodiments oral appliance 100 may be configured to be molded to respective portions, but not all, of the upper and/or lower dental arches.

In certain embodiments, deformable blank 500 may be formed entirely or substantially from a deformable material. For example, deformable blank 500 may be formed from a suitable thermoplastic polymer and suitable fillers, stabilizers, coloring agents, antioxidants, antimicrobial agents, and/or other materials.

In certain embodiments, deformable blank 500 may include, possibly in addition to one or more other materials, one or more of the thermoplastic polycaprolactone polymers or other aliphatic polyesters described in U.S. Pat. Nos. 4,784,123 and 5,112,225 and product literature of UNION CARBIDE CORPORATION. One or more polycaprolactone polymers may have the formula:

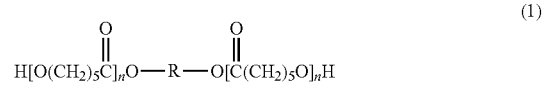

$$H[O(CH_2)_5C]_nO\text{---}R\text{---}O[C(CH_2)_5O]_nH \quad (1)$$

where R is an aliphatic hydrocarbon and n may range between approximately 300 to approximately 650. However, any suitable polycaprolactone polymer may be used.

For example, deformable blank 500 may be formed wholly or partially from one or more of TONE P-700, TONE P-767, or TONE P-787 polycaprolactone polymers manufactured by UNION CARBIDE CORPORATION, singly or in any combination. In a particular example, deformable blank 500 may include approximately thirty parts by volume of TONE P-700 and sixty parts by volume of TONE P-767, together with approximately ten parts by volume of one or more other polymers, depending upon the application and particular needs.

TONE polycaprolactone polymers are described in U.S. Pat. Nos. 4,784,123 and 5,112,225 and product literature of UNION CARBIDE CORPORATION as including homopolymers, block copolymers, graft copolymers, or other polymers containing epsilon-caprolactone. Polymerization may be initiated using a diol, for example and without limitation, ethylene glycol, diethylene glycol, neopentyl glycol, butane diol, hexane diol, or any other appropriate diol. The diol may have the formula:

$$HO\text{---}R\text{---}OH \quad (2)$$

where R is an aliphatic hydrocarbon. In general, polycaprolactone polymers may display desirable dimensional stability and thermoplasticity during cooling, biocompatibility, and a variety of other characteristics making them suitable for use in forming embodiments of oral appliance 100.

Particular oral appliances 100 formed wholly or partially from one or more polycaprolactone polymers may provide a number of desirable features. For example, particular oral appliances 100 formed from one or more polycaprolactone polymers may be inserted into the user's mouth while in a deformable state, molded to particular features of the user's mouth while in a deformable state, and transitioned from a deformable state to a substantially non-deformable state while in the user's mouth, all without harming the user. Additionally, particular oral appliances 100 formed from one or more polycaprolactone polymers may be sufficiently thin so as to be positioned within a user's mouth in a manner that enables the user's rearmost teeth to approximate centric occlusion. For example, particular oral appliances 100 formed from one or more polycaprolactone polymers may be thinned at certain locations to 0.1 mm or less and may further be capable of retaining a desired shape of the thinnest locations while being exposed to body temperature. These example properties may be distinguished from other types of materials that must be shaped outside of the mouth because of potentially toxic outgases, liquids, particulates, harmful temperatures, and/or ultra-violet exposure associated with other molding processes. Additionally, the above properties provided by some polycaprolactone polymers may be distinguished from other materials that are significantly more malleable at body temperature, that are not deformable at temperatures safe for use in a user's mouth, and/or that cannot readily be thinned to 1 mm or less and still retain a substantially non-deformable shape.

Figure 6:
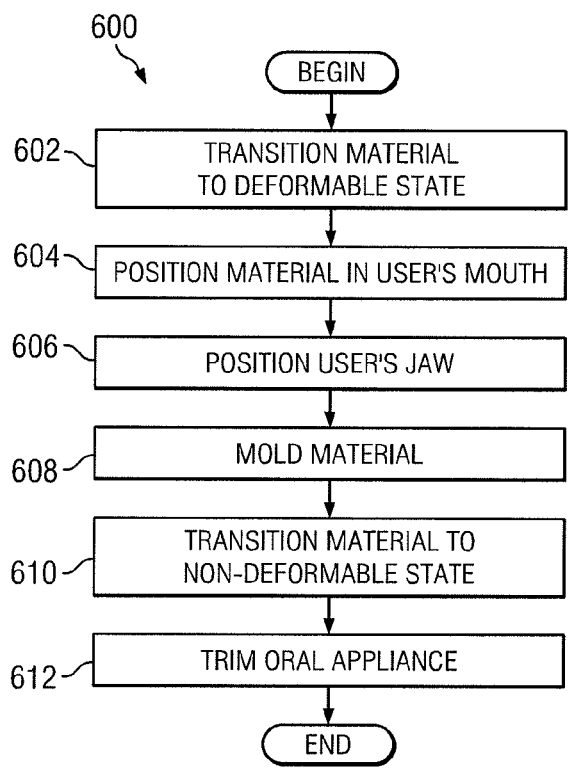
FIG. 6 is a flowchart illustrating example steps for forming the oral appliance of FIG. 1 through 4 according to an example embodiment.

FIG. 6 is a flowchart 600 illustrating example steps for forming a custom-fit oral appliance 100 for repositioning the jaw of a particular user according to one embodiment. In this example, flowchart 600 generally includes transitioning a thin sheet of material 500 to a deformable state, positioning the user's jaw in a substantially centric occlusal position, molding the thin material 500 around at least respective portions of upper and lowers dental arches of a mouth, transitioning the molded thin material 500 to a substantially non-deformable state, and trimming the thin material 500.

In step 602, the thin sheet of material 500 is transitioned to a deformable state. In certain embodiments, the thin sheet of material 500 may be transitioned to a deformable state by heating the thin material 500 to a suitable temperature. For example, thin material 500 may be heated by submersing it within water and heating the water to a temperature within the range of approximately 140 degrees Fahrenheit to boiling; however, any suitable temperature may be used that facilitates molding thin material 500. In a particular embodiment, thin material 500 is heated to approximately 160 degrees Fahrenheit, which in some cases may be a suitable temperature for readily molding thin material 500 while not being too hot for insertion of thin material 500 into a user's mouth.

In step 604, thin material 500 is positioned in a user's mouth. In a particular embodiment, thin material 500 may be inserted into a user's mouth and positioned such that it covers all or a portion of the user's upper and/or lower dental arches.

In step 606, the user's jaw is positioned in a substantially centric occlusal position. In certain embodiments, a user's jaw may be positioned such that the upper and lower dental arches are aligned according to the user's a natural bite.

In step 608, thin material 500 is molded around at least respective portions of upper and lower dental arches of a mouth. In certain embodiments, a user may bite down upon thin material such that portions of the upper and lower dental arches of the mouth form respective dental impressions of the user's upper and lower dentitions (bite register) on opposite sides of thin material 500. According to one embodiment, a user may bite down on thin material 500 such that the rearmost teeth of the user's upper and lower dental arches are spaced apart approximately 0.1 mm or less. As part of the molding step 604, a user may press deformable blank 500 against at least a portion of the user's pallet. Additionally, portions of deformable blank 500 may be manipulated around the upper dental arch to facilitate formation of the example shapes shown in FIGS. 1-4. In particular embodiments, a user may achieve an optimal fit and tighter seal by sucking air and/or moisture out of the mouth.

In step 610, thin material 500 is transitioned to a substantially non-deformable state. In certain embodiments, at least some of the transitioning process of step 610 may be performed while thin material 500 is molded within a user's mouth and by allowing thin material 500 to cool to the user's body temperature. In particular embodiments, thin material 500 may also be transitioned to a substantially non-deformable state by removing the molded thin material 500 from the user's mouth and exposing the molded thin material 500 to room temperature, or a cooler temperature, for a sufficient amount of time to allow thin material 500 to harden. In certain embodiments, one to two minutes of cooling at body temperature may be sufficient to allow the molded deformable blank 500 to transition to a substantially rigid, non-deformable state. Particular thin materials 500 formed from one or more polycaprolactone polymers may be capable of retaining a substantially non-deformable shape over time even after multiple uses within the user's mouth. This property may be distinguished from particular boil-and-bite mouth guards that are substantially malleable at room temperature and/or at body temperature.

In step 612, thin material 500 may be trimmed for optimal shape. In particular embodiments, thin material 500 may be trimmed to avoid contact with the user's soft pallet when positioned in the user's mouth. In certain embodiments, thin material 500 may be trimmed such that portions of the labial surfaces of a user's upper dental arches are exposed when the user bites down on thin material 500, thereby avoiding contact by thin material 500 with the user's gums. In certain embodiments, sharper edges of oral appliance 100 may be trimmed and/or smoothed to mitigate injury or discomfort to the user.

To assist in describing the features and interactions of certain components, relational terms have been used. For example, certain components have been described as being upper or lower components. It should be understood that these terms have been used to describe example implementations and are not intended to limit the scope of the claimed invention. To the contrary, in alternative embodiments, the spatial location of one or more of the components described may be reversed or altered.

The example methods disclosed herein may include more, fewer, or other steps. For example, in alternative embodiments oral appliance 100 may be formed by molding a heated deformable blank 500 against a plaster mold (or some other type of mold) of a user's teeth. Additionally, steps may be performed in any suitable order. For example, in alternative embodiments a sheet of thin material 500 may be at least partially molded to a user's lower dentition before the user bites down and/or before the user's jaw is positioned in a substantially centric occlusal position. In particular embodiments, all or a portion of the steps disclosed herein may be wholly or partially performed by a user (e.g., a wearer of the oral appliance) and/or by someone else (e.g., a dentist, an orthodontist automated, an oral hygienist, a parent, etc.). As used in this document, "each" refers to each member of a set or each member of a subset of a set.

Although the present invention has been described in several embodiments, a myriad of changes, substitutions, variations, transformations, and modifications may be suggested to one skilled in the art, and it is intended that the present invention encompass such changes, substitutions, variations, transformations, and modifications as fall within the scope of the appended claims.

What is claimed is:

1. A method for forming a custom-molded oral appliance for positioning a user's jaw proximate to centric occlusion, comprising:
   heating a thin sheet of material comprising a polycaprolactone polymer;
   positioning the thin sheet of material within the user's mouth;
   positioning the user's jaw proximate to centric occlusion;
   molding the thin sheet of material around at least respective portions of the user's upper and lower dental arches such that each of the respective portions of the user's upper and lower dental arches form respective impressions on opposite sides of the thin sheet of material; and
   transitioning the thin sheet of material to a substantially non-deformable state;
   wherein the thin sheet of material is molded around at least respective portions of the user's upper and lower dental arches, such that:
      a portion of the thin sheet of material molded around at least one molar is thinner than 0.1 millimeter; and
      at least a portion of the thin sheet of material is thicker than 2 mm.

2. The method of claim 1, further comprising trimming the thin sheet of material.

3. The method of claim 1, wherein heating the thin sheet of material further comprises heating the thin sheet of material to a temperature of at least 140 degrees Fahrenheit.

4. The method of claim 1, wherein transitioning the thin sheet of material to the non-deformable state further comprises allowing the thin sheet of material to cool to 100 degrees Fahrenheit or less.

5. The method of claim 1, wherein the thin sheet of material is substantially non-deformable at approximately 100 degrees Fahrenheit.

6. The method of claim 1, wherein the at least the portion of the thin sheet of material transitioned to the non-deformable state comprises impressions formed on opposite sides of the thin sheet of material by respective occlusal surfaces of the upper and lower dental arches of the mouth.

7. A custom-fit oral appliance for positioning a user's jaw proximate to centric occlusion, comprising:
a molded sheet of material comprising a polycaprolactone polymer, the molded sheet of material being in a substantially non-deformable state and being molded to conform to features of a user's mouth such that the molded sheet of material comprises:
bite impressions of the upper and lower dentitions of the user's mouth;
an impression of a portion of the user's palate; and wherein the thin sheet of material is molded around at least respective portions of the user's upper and lower dental arches such that:
a portion of the thin sheet of material molded around at least one molar is thinner than 0.1 millimeters; and at least a portion of the thin sheet of material is thicker than 2 mm.

8. The custom-fit oral appliance of claim 7, wherein the at least the portion of the molded sheet of material comprises impressions formed on opposite sides of the molded sheet of material by respective occlusion surfaces of the upper and lower dental arches of the user's mouth.

9. A method for forming a custom-molded oral appliance for positioning a user's jaw proximate to centric occlusion, comprising:
heating, a thin sheet of material comprising a polycaprolactone polymer;
positioning the thin sheet of material within the user's mouth;
positioning the user's jaw proximate to centric occlusion;
molding the thin sheet of material around at least respective portions of the user's upper and lower dental arches such that each of the respective portions of the user's upper and lower dental arches form respective impressions on opposite sides of the thin sheet of material, wherein molding the heated thin sheet of material around at least respective portions of the user's upper and lower dental arches further comprises:
biting down on the heated thin sheet of material;
pressing the heated thin sheet of material against a palate of the mouth; and
pressing the heated thin sheet of material around the upper dental arch of the mouth; and
transitioning the thin sheet of material to a substantially non-deformable state;
wherein at least a portion of the thin sheet of material transitioned to the non-deformable state is thinner than 0.1 millimeters.

10. A method for forming a custom-molded oral appliance for positioning a user's jaw proximate to centric occlusion, comprising:
heating a thin sheet of material comprising a polycaprolactone polymer;
configuring the thin sheet of material to be positioned within the user's mouth to receive bite impressions of the user's upper and lower dentitions of the mouth, to be pressed against a portion of the user's palate, and to be pressed around portions of the user's upper dental arch;
positioning thin sheet of material within the user's mouth;
positioning the user's jaw proximate to centric occlusion;
molding the thin sheet of material around at least respective portions of the user's upper and lower dental arches such that each of the respective portions of the user's upper and lower dental arches form respective impressions on the opposite sides of the thin sheet of material; and
transitioning the thin sheet of material to a substantially non-deformable state;
wherein at least a portion of the thin sheet of material transitioned to the non-deformable state is thinner than 0 1 millimeters.

11. A method for forming a custom-molded oral appliance for positioning a user's jaw proximate to centric occlusion, comprising:
heating a thin sheet of material to a temperature of at least 140 degrees Fahrenheit, the thin sheet of material comprising a polycaprolactone polymer;
positioning the thin sheet of material within the user's mouth;
positioning the user's jaw proximate to centric occlusion;
molding the thin sheet of material around at least respective portions of the user's upper and lower dental arches such that each of the respective portions of the user's upper and lower dental arches form respective impressions on opposite sides of the thin sheet of material; and
transitioning the thin sheet of material to a substantially non-deformable state by allowing the thin sheet of material to cool to 100 degrees Fahrenheit or less, wherein the thin sheet of material is substantially non-deformable at approximately 100 degrees Fahrenheit; and wherein the thin sheet of material is molded around at least respective portions of the user's upper and lower dental arches, such that:
a portion of the thin sheet of material molded at least one molar is thinner than 0.1 millimeters; and,
at least a portion of the thin sheet of material is thicker than 2 mm.

12. The method of claim 11, further comprising trimming the thin sheet of material.

13. The method of claim 11, wherein the at least the portion of the thin sheet of material transitioned to the non-deformable state comprises impressions formed on opposite sides of the thin sheet of material by respective occlusion surfaces of the upper and lower dental arches of the mouth.

14. A method for forming a custom-molded oral appliance for positioning a user's jaw proximate to centric occlusion, comprising:
heating a thin sheet of material to a temperature of at least 140 degrees Fahrenheit, the thin sheet of material comprising a polycaprolactone polymer;
configuring the thin sheet of material to be positioned within the user's mouth to receive bite impressions of the user's upper and lower dentitions of the mouth, to be pressed against a portion of the user's palate, and to be pressed around portions of the user's upper dental arch;

positioning the thin sheet of material within the user's mouth;

positioning the user's jaw proximate to centric occlusion;

molding the thin sheet of material around at least respective portions of the user's upper and lower dental arches such that each of the respective portions of the user's upper and lower dental arches form respective impressions on opposite sides of the thin sheet of material; and transitioning the sheet of material to a substantially non-deformable state by allowing the thin sheet of material to cool to 100 degrees Fahrenheit or less, wherein the thin sheet of material is substantially non-deformable at approximately 100 degrees Fahrenheit; and wherein at least a portion of the thin sheet of material transitioned to the non-deformable state is thinner than 0.1 millimeters.

15. A method for forming a custom-molded oral appliance for positioning a user's jaw proximate to centric occlusion, comprising:

heating a thin sheet of material to a temperature of at least 140 degrees Fahrenheit, the thin sheet of material comprising a polycaprolactone polymer;

positioning the thin sheet of material within the user's mouth;

positioning the user's jaw proximate to centric occlusion;

molding the thin sheet of material around at least respective portions of the user's upper and lower dental arches such that each of the respective portions of the user's upper and lower dental arches form respective impressions on opposite sides of the thin sheet of material, wherein molding the heated thin sheet of material around at least respective portions of the user's upper and lower dental arches further comprises:

biting down on the heated thin sheet of material;

pressing the heated thin sheet of material against a palate of the mouth; and pressing the heated thin sheet of material around the upper dental arch of the mouth; and transitioning the sheet of material to a substantially non-deformable state by allowing the thin sheet of material to cool to 100 degrees Fahrenheit or less, wherein the thin sheet of material is substantially non-deformable at approximately 100 degrees Fahrenheit; and wherein at least a portion of the thin sheet of material transitioned to the non-deformable state is thinner than 0.1 millimeters.

* * * * *